United States Patent [19]

Rhoades et al.

[11] Patent Number: 5,082,444
[45] Date of Patent: Jan. 21, 1992

[54] PORTABLE PRESSURIZED PULSED ORALCAVITY CLEANER

[76] Inventors: Clark J. Rhoades, 181 Tweed Blvd., Nyack, N.Y. 10960; Stephen J. Gambuti, 616 Ramapo Ave., Pompton Lakes, N.J. 07442

[21] Appl. No.: 335,687

[22] Filed: Apr. 10, 1989

[51] Int. Cl.$^5$ .................................... A61G 17/02
[52] U.S. Cl. ............................. 433/80; 239/389; 433/89
[58] Field of Search ............. 433/80, 89; 128/66, 128/62 A; 239/337, 101, 381, 382, 389, 486; 229/89; 220/85 H, DIG. 21; 206/446, 63.5

[56] References Cited

U.S. PATENT DOCUMENTS

| | | | |
|---|---|---|---|
| 3,116,947 | 1/1964 | Brownrigg | 220/85 H |
| 3,118,612 | 1/1964 | Abplanalp | 239/337 |
| 3,391,696 | 7/1968 | Woodward | 128/232 |
| 3,480,009 | 11/1969 | Sinai | 128/66 |
| 3,624,219 | 11/1971 | Perlitsch | 424/7 |
| 3,883,074 | 5/1975 | Lambert | 239/101 |
| 4,015,779 | 4/1977 | Kwok | 239/381 X |
| 4,276,880 | 7/1981 | Malmin | 433/80 X |
| 4,365,752 | 12/1982 | Waisbren | 239/381 |
| 4,457,711 | 7/1984 | Maloney | 433/82 |
| 4,564,005 | 1/1986 | Marchand | 128/66 |
| 4,620,528 | 11/1986 | Arraval | 128/62 A |

FOREIGN PATENT DOCUMENTS

| | | | |
|---|---|---|---|
| 14652 | 7/1933 | Australia | 68.9/87.7 |
| 2819404 | 11/1979 | Fed. Rep. of Germany | 433/80 |
| 3146729 | 7/1983 | Fed. Rep. of Germany | 433/80 |
| 3203723 | 8/1983 | Fed. Rep. of Germany | 433/89 |
| 1424902 | 2/1976 | United Kingdom | 433/80 |

*Primary Examiner*—Robert P. Swiatek
*Assistant Examiner*—Nicholas D. Lucchesi
*Attorney, Agent, or Firm*—John H. Crozier

[57] ABSTRACT

The present invention relates to a portable, self powered, oral cavity cleaner that produces a pulsed stream of fluid to clean the teeth, and areas around the gums and teeth. It is powered by compressed gas contained in a container along with the fluid to be dispensed, and has a valve that produces a pulsed stream.

The fluid in the pressurized unit could contain some or all of the following: breath freshener, plaque inhibitor or dissolving agent, bactericidal and bacteriostatic ingredients. It should also exhibit the ability to be swallowed so that spitting it out might be obviated while leaving the mouth feeling refreshed.

The stream is directed by a tube that has an angle and an articulated joint that is leak proof and snaps together for assembly. The dispensing tube, articulated joint, and pulsating valve are protected by a hygienic cover which rotates respective to the container to expose the tube. The pulsating valve, hygienic cover and dispensing tube may be reused.

In another embodiment the pulsating valve fits onto a bottle of soda enabling an individual to clean the teeth using the fluid and the dissolved gas in the soda bottle to provide the pressure and working fluid to clean the teeth.

18 Claims, 9 Drawing Sheets

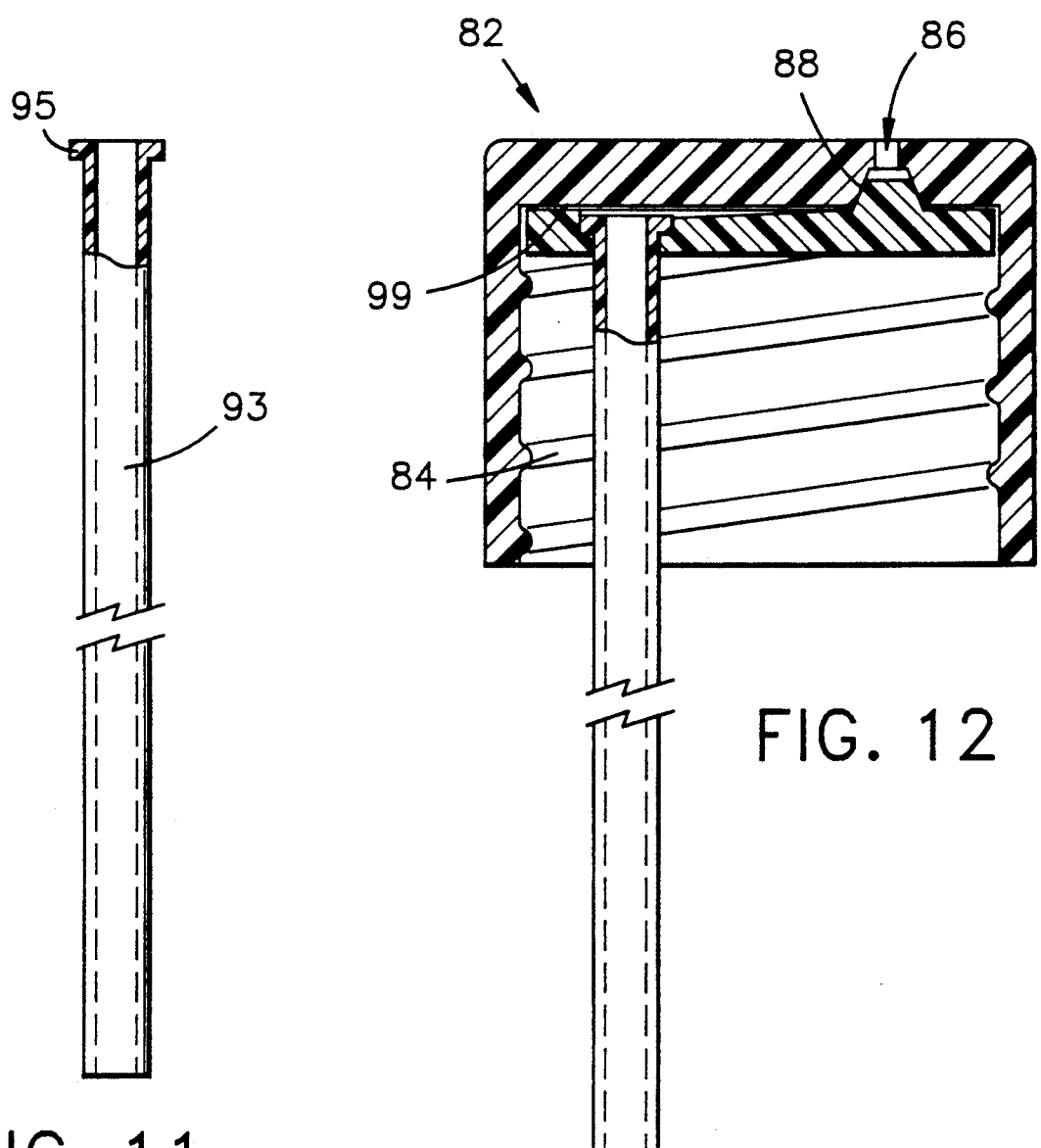

PORTABLE PRESSURIZED PULSED ORALCAVITY CLEANER

BACKGROUND

1. Field of Invention

The present invention relates to a portable, self powered, oral cavity cleaner that produces a pulsed stream of fluid to clean the teeth, and areas around the gums and teeth.

2. Background

It is widely recognized that regular cleaning of the teeth, stimulation of the gums, and removal of particulate matter between the teeth, is necessary for a healthy oral cavity.

Tooth brushes are good tools for cleaning teeth. Unless they are protected, they gather dirt when put into a purse or pocket and become unappealing to use and might cause a health hazard. Some tooth brushes come equipped with a carrying case but the tooth brushes must be thoroughly cleaned and dried before putting them into a carrying case or the tooth brushes will provide a breeding ground for bacteria and could be detrimental to one's health.

One known method developed to clean between the teeth and stimulate the gums, was a high pressure steady stream of water, but this was found damaging to the gums. Then, the Water Pick was developed with its pulsated stream of water. A stream that pulses between 1000 and 1600 times a minute has been found most helpful to the gums, stimulating the gum tissue, improving the blood flow and the elasticity of the tissue.

The Water Pick has been successfully used for many years. It suffers from a number of serious drawbacks: expense, bulk and weight. Moreover, it requires a water supply. Because of these shortcomings, Water Picks often are not carried by people when they leave their homes even when they would prefer to use them away from home. One object of this invention is to solve this problem.

The device of the present invention is a self-contained pressurized unit having the means to pulsate a directed stream of fluid. It is portable and inexpensive. It is small enough to be carried in a pocket or purse. It has parts that can be transferred from one pressurized container to another when the first is emptied. This will reduce the cost to the user.

The fluid in the pressurized unit could contain some or all of the following: breath freshener, plaque inhibitor or dissolving agent, bactericidal and bacteriostatic ingredients. It should also exhibit the ability to be swallowed so that spitting it out might be obviated while leaving the mouth feeling refreshed.

One of the embodiments of this invention may be secured in place of a bottle cap on carbonated beverages. Users might have a meal with a bottle of carbonated soda as a beverage. At the end of the meal they would place the device on the bottle, give a shake, turn the bottle upside down, and then spray into their mouths, removing the residue from their meals. Not only would there be a pulsed jet but each pulse would be bubbles of carbon dioxide that would have the further beneficial effect of foaming away the particles between the teeth.

Children might be encouraged to play with carbonated water or diet soda and use the device as a self powered "water pistol" and it is hoped that while playing they would squirt it into their mouths, to refresh themselves, thereby cleaning their teeth and learning the delight of a clean mouth.

Descriptions of previous attempts to answer the need of a portable, fluid utilizing, oral cleaning device include the following patents:

Australian patent No. 14,652/33 shows a device, refillable with both liquid and carbon dioxide cartridges. The device was complicated, expensive, and produced a solid jet of fluid that could be damaging to sensitive gums.

Another type of design is represented by U.S. Pat. Nos. 3,391,696 and 3,480,009. These patents described devices which are hand powered, portable and refillable. Neither device provides a pulsed stream with a cyclical rate of 1000 to 1600 pulses a minute, the optimal pulsed cycle for the maximum benefit for the gums. In addition they require hand coordination and flexibility that some users may lack.

U.S. Pat. No. 4,457,711 describes a pressurized container to spray out a liquid through a dispenser that acts as a scrubbing device. The spray is not pulsated.

U.S. Pat. No. 3,624,219 describes a device which discharges a single, small amount of plaque disclosing substance. It is not designed as a particle remover or a gum stimulator.

OBJECTS AND ADVANTAGES

One object of this invention is to provide a novel and improved oral hygiene device.

Another object of this invention is to provide a self powered oral hygiene device that is small enough to fit in a pocket or a purse.

Another object of this invention is to provide a truly portable oral hygiene device delivering a high cycle rate of pulsed fluid.

Another object of this invention to provide a portable, self powered oral hygiene device that will not leak or accidentally discharge while in the pocket or purse.

Another object of this invention is to allow those with physical impairments, who would otherwise not be able to clean their teeth and stimulate their gums, while away from home, to do so.

Another object of this invention is to provide a device that is inexpensive to produce.

Another object of this invention is to reduce the cost to the user by having a pulsating and directing device that can be easily removed from an empty pressurized container and attached to a full one.

Another object of this invention is to provide a device that is fun for children to use.

Another object of this invention to protect its applicator from coming into contact with the inside of the pocket or purse.

Another object of this invention is to give the consumer a varied choice of fluids to use in the device.

Another object of this invention is to give the consumer a device that can be used with easily available pressurized containers.

These and other and further objects of this invention will become apparent from the continued description and drawings which follow, in which:

BRIEF DESCRIPTION OF DRAWINGS

FIG. 10: is a cross sectional and oblique view of the flexible valve.

FIG. 11: is a cross sectional view of the pickup tube for the flexible valve.

FIG. 12: is a cross sectional view of the bottle cap and flexible valve and pickup tube.

REFERENCE NUMERALS IN DRAWINGS

List of Parts

Figure 1:
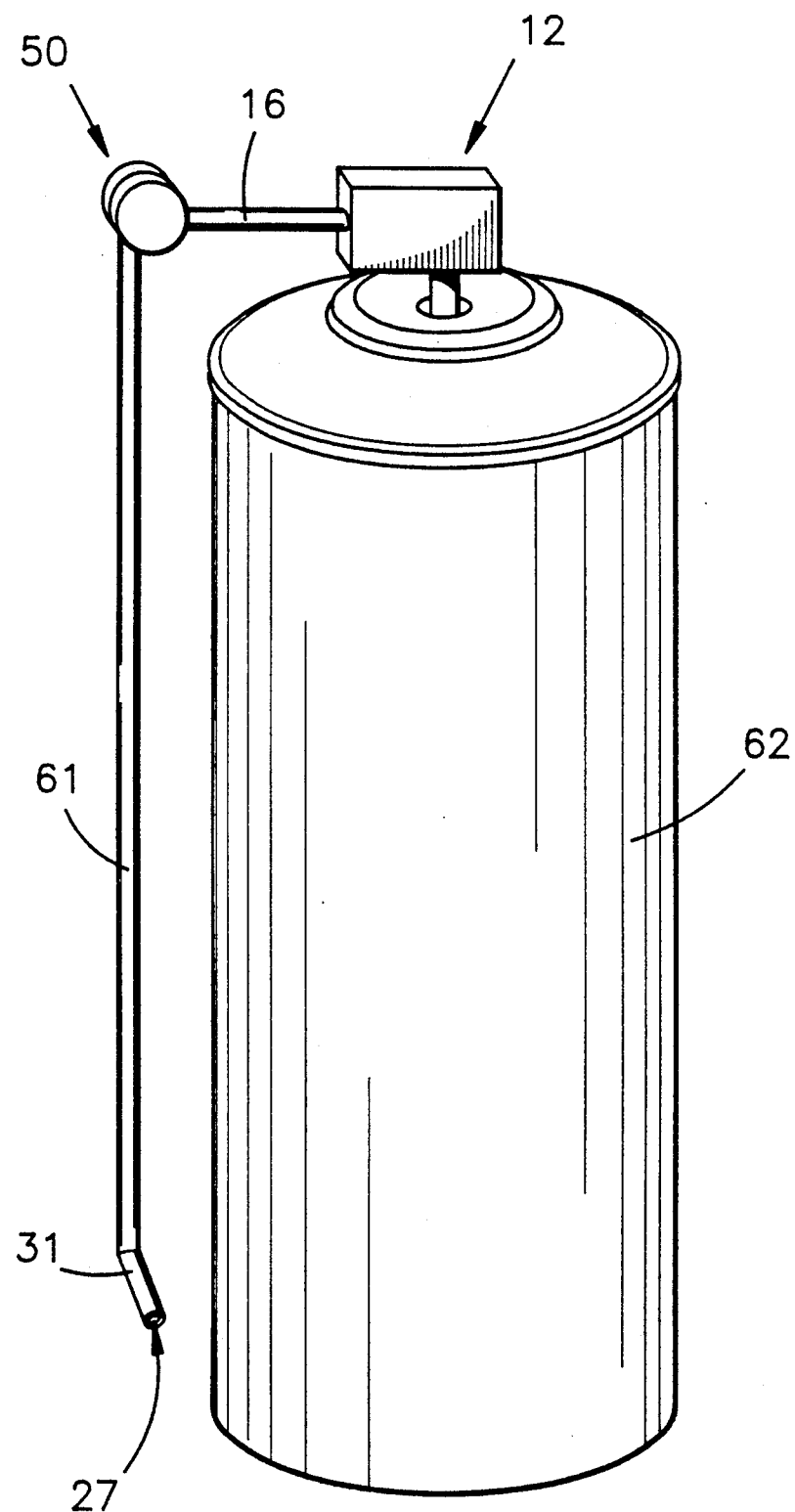
FIG. 1: is an external view showing the arrangement of parts for a top mounted pulsating valve with the pressurized container.

2: pulsating valve
3: cylinder end piece
4: bearing surface
6: rotor
8: fins
10: channel
12: pulsating valve body
14: end plate
15: tubular leg
16: rotatable thin tube
17: discharge port
18: sealing flange
19: port
20: retaining flange
22: low pressure zone
24: high pressure zone
26: tube
27: discharge port
28: channel
29: notch
30: angle
31: angle
32: bearing and sealing surface of the valve body
34: channel
36: port
38: flange
42: sealing plug
44: plug sealing surface
45: sealing washer for hollow projection
46: O ring
47: orifice for hollow projection
48: securing hooks
49: flange
50: leak resistant rotatable joint
52: male securing hooks
54: female securing hooks
56: common sealing surface
57: flat circular surface
58: common chamber
60: resilient points
61: applicator tube
62: pressurized container
70: sanitary shield
72: top of sanitary shield
73: bottom of sanitary shield
74: top lip of the container
76: bottom lip of the container
78: face of sanitary shield
80: opening in the top of the sanitary shield
82: bottle cap
84: threads
86: exit port
88: valve seat
90: pulsating flexible valve
91: notch
92: tapered plug
93: fluid pickup tube
94: flexible valve port
95: pickup tube flange
96: area where the depression formes
98: top of tapered plug
99: top inside surface of the bottle cap
102: pulsating valve
104: bearing surface
106: rotor
108: fins
110: channel
112: internal valve body
114: end plate
120: retaining flange
122: low pressure zone
124: high pressure zone
126: tube
128: channel
132: bearing and sealing surface
136: port
226: fluid pickup tube
228: channel
236: port
240: flange sealing surface
241: sealing plug
242: top of sealing plug
244: plug sealing surface
245: sealing washer for tube
246: O ring
247: orifice
248: securing hooks
249: flange.

DESCRIPTION OF THE PREFERRED EMBODIMENTS

Turning first to FIG. 1 which shows the relationship of the several parts of the device, it will be seen that the device comprises a pressurized container 62 on which a external pulsating valve body 12 is mounted. Extending from external pulsating valve body 12 is a rotatable thin tube 16 which is attached to the leak resistant rotatable joint 50 which is also connected to an applicator tube 61. Near the end of applicator tube 61 are an angle 31 and a discharge port 27 for discharging the treating fluid.

Figure 2:
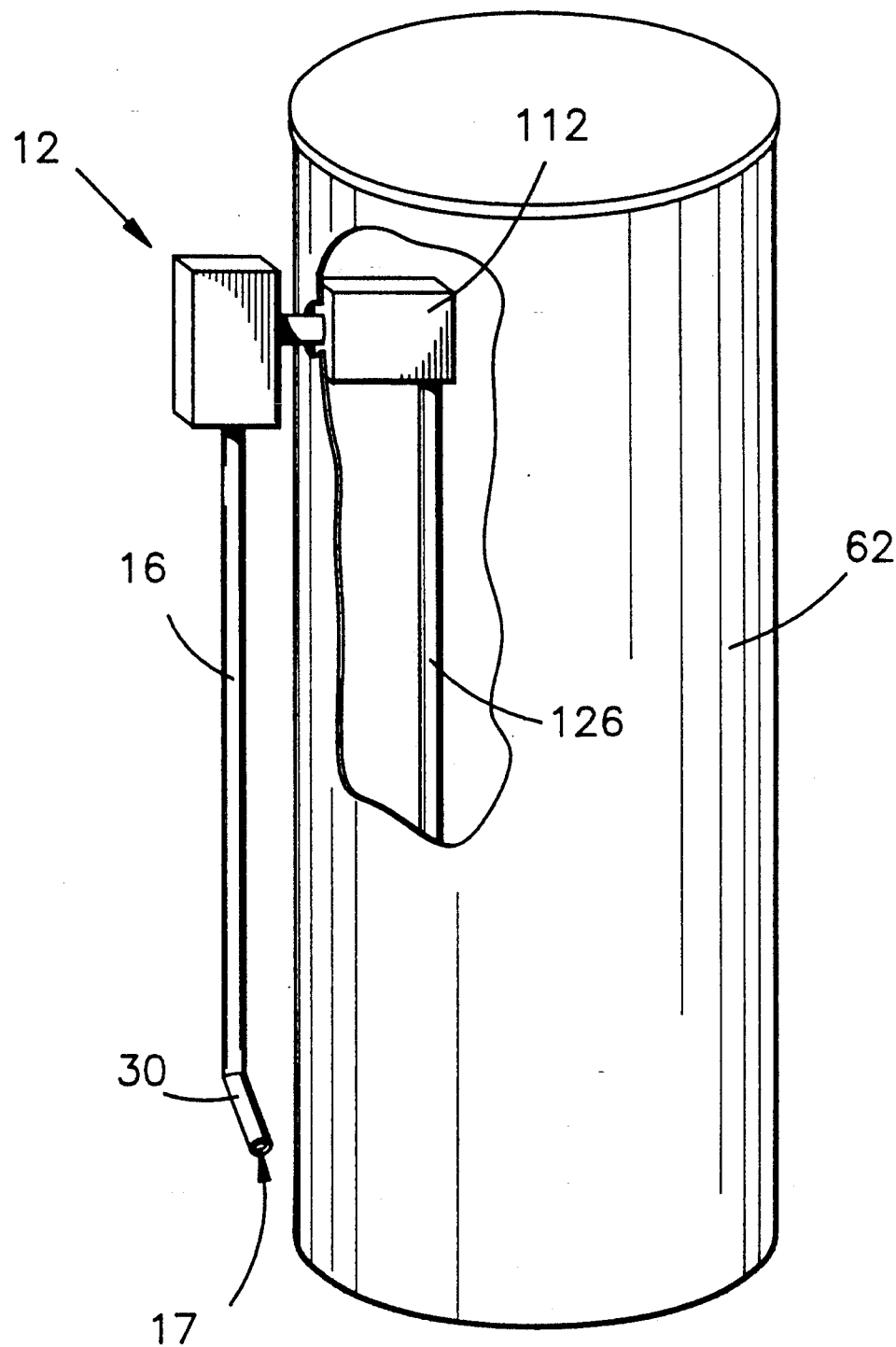
FIG. 2: is a cutaway view of a pressurized container showing the side mounted configurations for an external and internal pulsating valve.

FIG. 2 is a cutaway view of the pressurized container 62 showing two embodiments in which the pulsating valve body, either external 12 or internal 112, can be mounted on a side of the pressurized container. This configuration eliminates use of the leak resistant rotatable joint 50 of FIG. 1 and allows the rotatable thin tube 16 to lie flat against the side of the pressurized container 62. Near the discharge port 17 is an angle 30.

Figure 3:
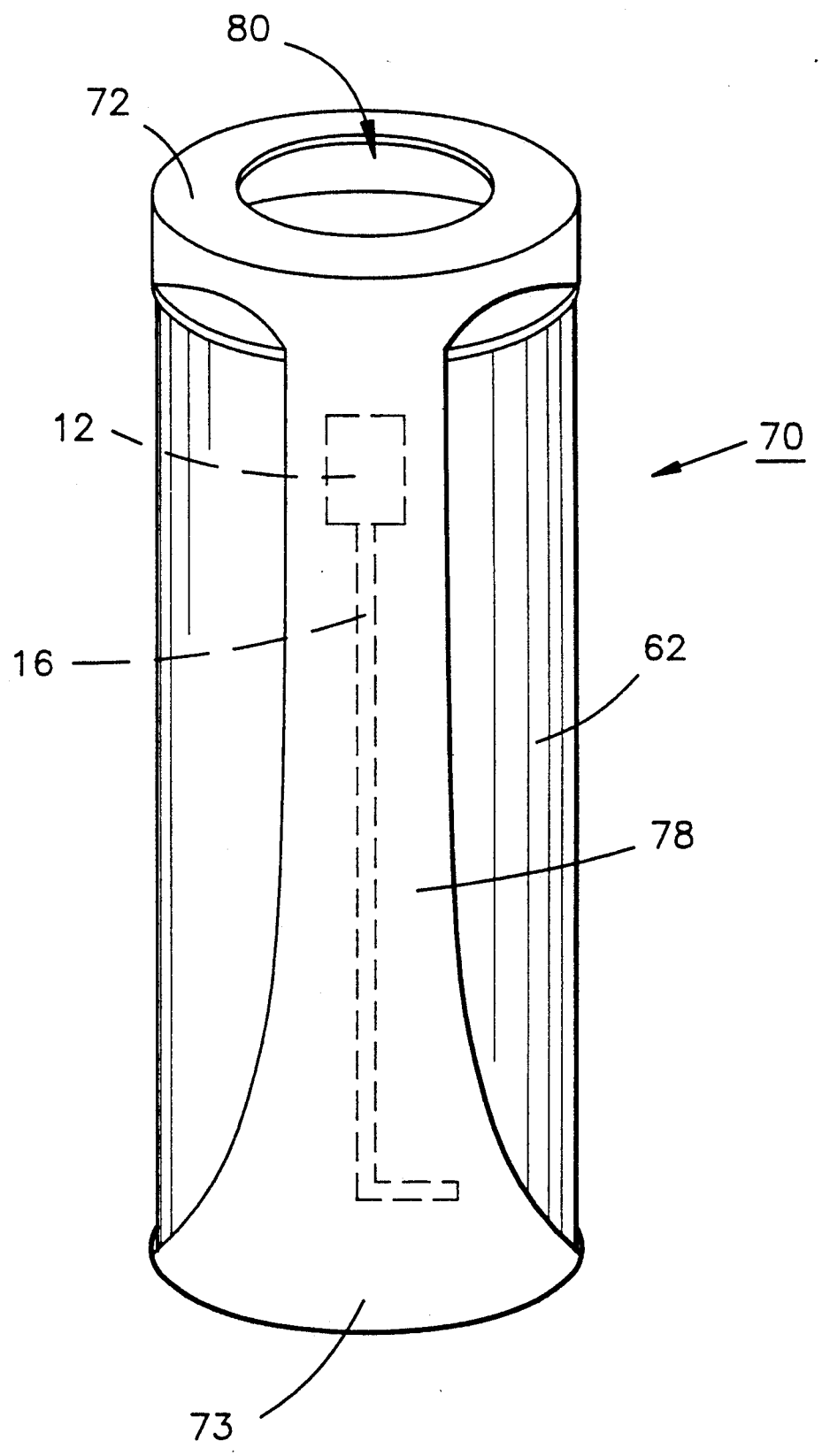
FIG. 3: is a frontal view showing the sanitary shield, a side mounted pulsating valve and the pressurized container.

FIG. 3 is a view showing a sanitary shield 70 and its relationship to the pressurized container 62 and to a side mounted external pulsating valve body 12 with a rotatable thin tube 16 secured against the side of the pressurized container and shielded from direct contact with dirty surfaces.

Figure 4:
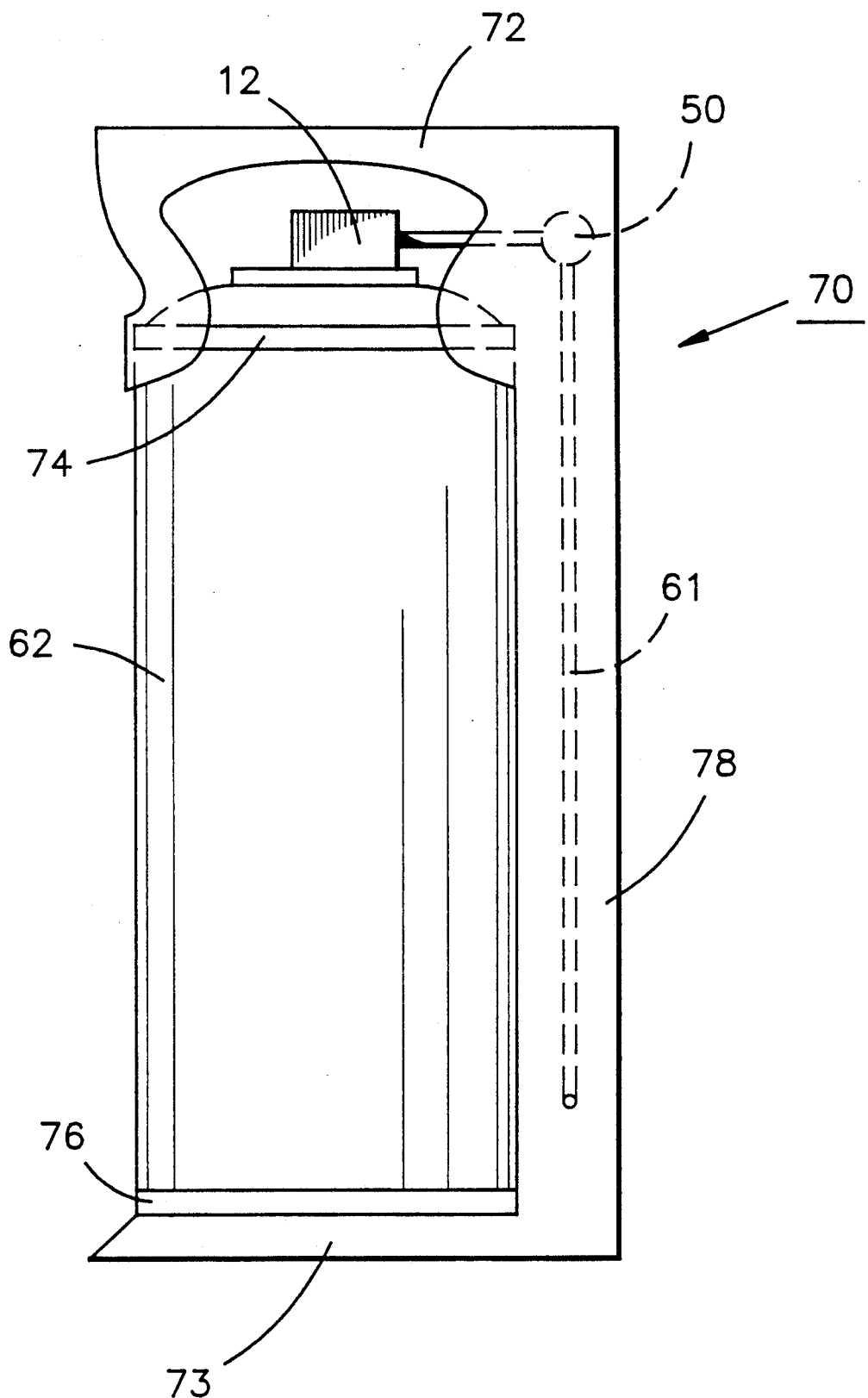
FIG. 4: is a side view showing the sanitary shield with a top mounted pulsating valve.

FIG. 4 is a side view showing a pressurized container 62 and a sanitary shield 70. The pressurized container 62 has a top mounted external pulsating valve body 12. The pressurized container is held in place by a top lip 74 and a bottom lip 76 of the sanitary shield 70. Friction between the pressurized container 62 and the sanitary shield 70 keep it in place until the user grasps the shield in one hand and rotates the can within the lips 74 and 76 to expose the applicator tube. A finger, placed through an opening 80 in the top of the sanitary shield 70 (shown in FIG. 3) operates external pulsating valve body 12.

FIGS. 3 and 4 show the device assembled with a sanitary shield 70 snapped onto the pressurized container 62 in such fashion as to protect the external pulsating valve body 12 from accidental damage and the outlet from contamination by dirt or other foreign material when the device is stored in a purse or pocket. The sanitary shield 70 comprises a face 78 connecting a base or bottom portion 73 with a cap or top portion 72. An opening 80 in top 72 of the sanitary shield is provided for pressurized containers in which the outlet valve is mounted on the top of the pressurized container. The pressurized container 62 is held in place in the sanitary shield 70 in two places. The bottom of the shield 73 includes a bottom lip 76 and the top of the shield 72 includes a top lip 74. The pressurized container 62 may be rotated relative to shield 70 by hand movement.

The manufacturer or user places the pressurized container into the sanitary shield by flexing the face of the shield 78 so that the space between top lip 74 and bottom lip 76 is sufficient for pressurized container 62 to be inserted between the lips.

An advantage of this design is that the shield 70, external external pulsating valve body 12, and the applicator parts 16, 50, and 61 are reusable by the consumer, thereby reducing the reuse cost to only the purchase of the pressurized container.

Figure 5:
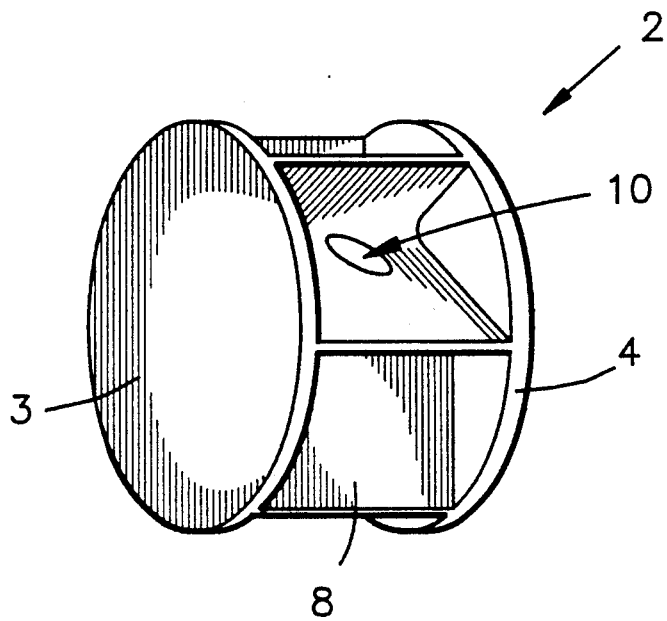
FIG. 5: is a perspective view of the pulsating valve.
Figure 6:
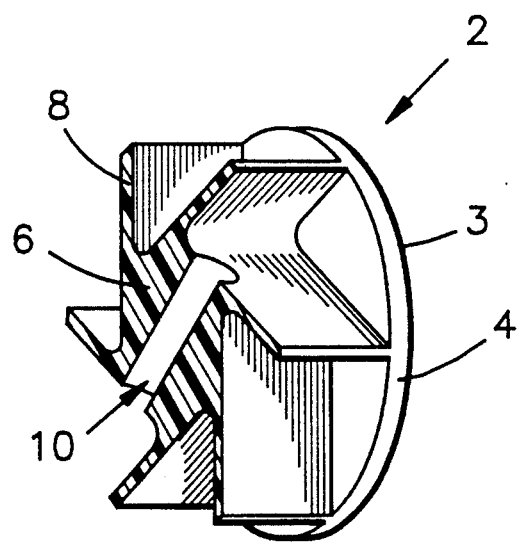
FIG. 6: is a view partly in perspective and partly in cross section of the pulsating valve.
Figure 7:
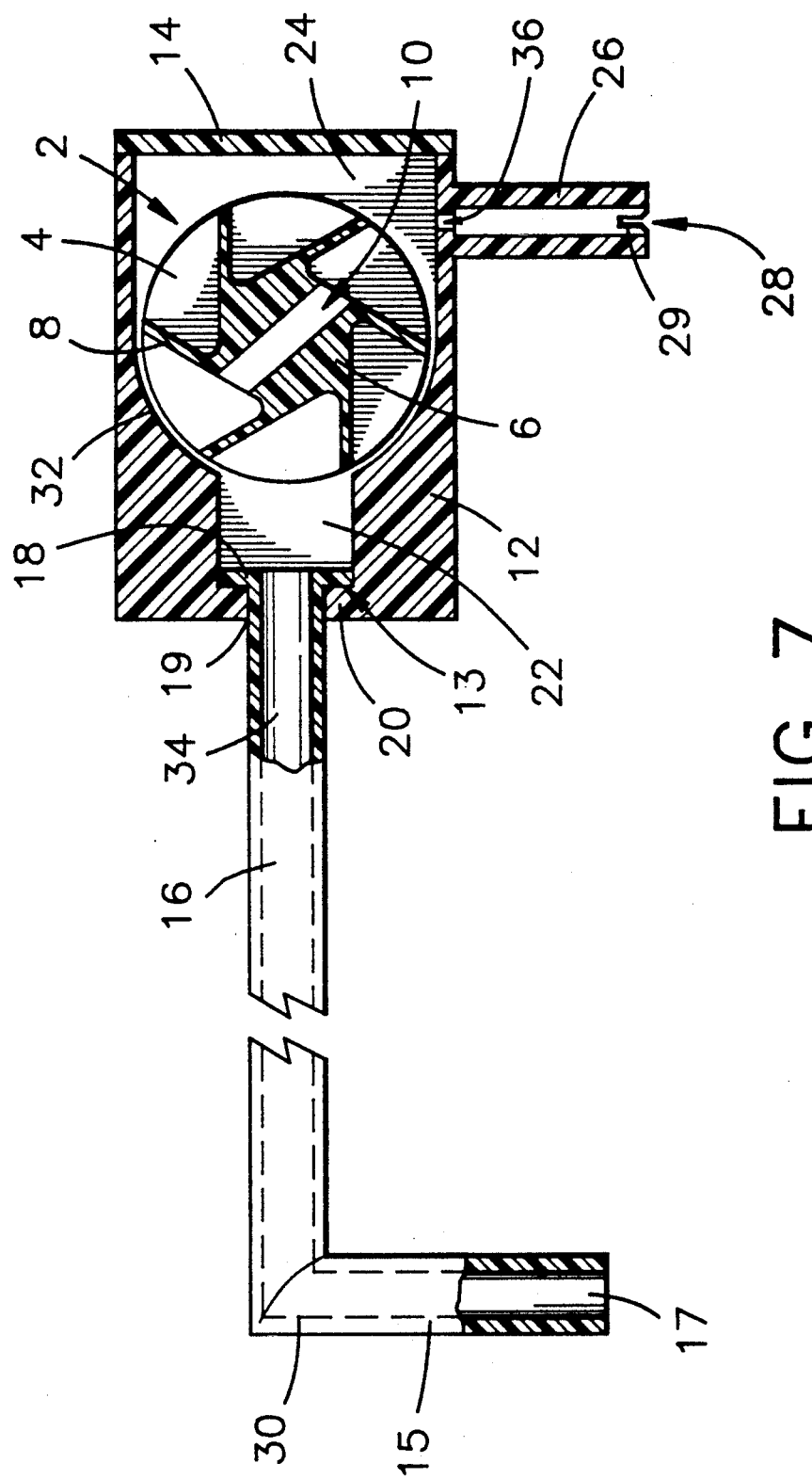
FIG. 7: is a cross section of the external valve body and parts.

FIGS. 5, 6, and 7 show one form of external pulsating valve body 12 which is externally mounted. As shown one end of external pulsating valve body 12 is sealed by an end plate 14, which is secured to the valve body during manufacturing after the rotatable thin tube 16 and a pulsating valve 2 have been inserted into pulsating valve body 12. External pulsating valve body 12 provides a housing for a pulsating valve 2 which is mounted for rotation on a bearing and sealing surface 32 within the external pulsating valve body 12.

Pulsating valve 2 consist of two circular end pieces 3, connected to each other by a rotor 6. The outer surface of the two end pieces 3 is the bearing surface 4 for valve 2. Pulsating valve 2 is provided with fins 8 along its periphery of the rotor and are attached to the end pieces 3 and the rotor 6 by any suitable means. At least one channel 10 extends transversely through the center axis of the rotor 6 (see FIG. 6).

A port 36 in the valve body communicates with channel 28 in tube 26, extending from the valve body. Tube 26 constitutes an inlet in external pulsating valve body 12 to admit the contents of pressurized container 62 into valve 2. Tube 26 connects to the discharge valve of pressurized container 62 or a conventional aerosol can. Tube 26 terminates with a notch 29 which cooperates with the valve on the pressurized container 62.

A rotatable thin tube 16 extends into the external pulsating valve body 12 through a port 19 in one wall of the external pulsating valve body 12. Rotatable thin tube 16 is provided with sealing flange 18 at the end of the tube where it extends through wall 13 and into the external pulsating valve body 12. The wall 13 of the body defines a retaining flange 20 within the external pulsating valve body 12. Adjacent to port 36 is a high pressure zone 24 in the valve body and adjacent to port 19 is a low pressure zone 22 in the valve body. Rotatable thin tube 16 has a tubular leg 15 extending at an angle 39 to rotatable thin tube 16, terminating in a discharge port 17.

The tube 26, is configured to connect with the valve opening of a pressurized container 62 or a conventional aerosol can. When the external pulsating valve body 12 is depressed, the tube 26 activates a valve in the pressurized container 62. The fluid under pressure is directed through notch 29 and up channel 28, enters the external pulsating valve body 12 at inlet port 36, and strikes the fins 8, causing the pulsating valve 2 to rotate. The fins 8 seal against the bearing and sealing surface 32 of the external pulsating valve body 12 creating a high pressure zone 24 in the region where fluid enters the valve body and a low pressure zone 22 near the area where the fluid exits the external pulsating valve body 12 through the rotatable thin tube 16.

The pulsating valve 2 has a bearing surface 4 which fits snugly against the bearing and sealing surface 32 of the valve body. The pulsating valve 2 is pressed against the bearing and sealing surface 32 by the high pressure in the zone 24.

The majority of fluid passes through the channel 10 and enters the low pressure zone 22. The pressure of this fluid presses the sealing flange 18, against the retaining flange 20. The fluid enters the channel 34 in the rotatable thin tube 16. The fluid is then directed by the angle 30 to the discharge port 17 which facilitates the directing of the pulses of fluid to strike and clean the teeth and the areas between the teeth.

Figure 8:
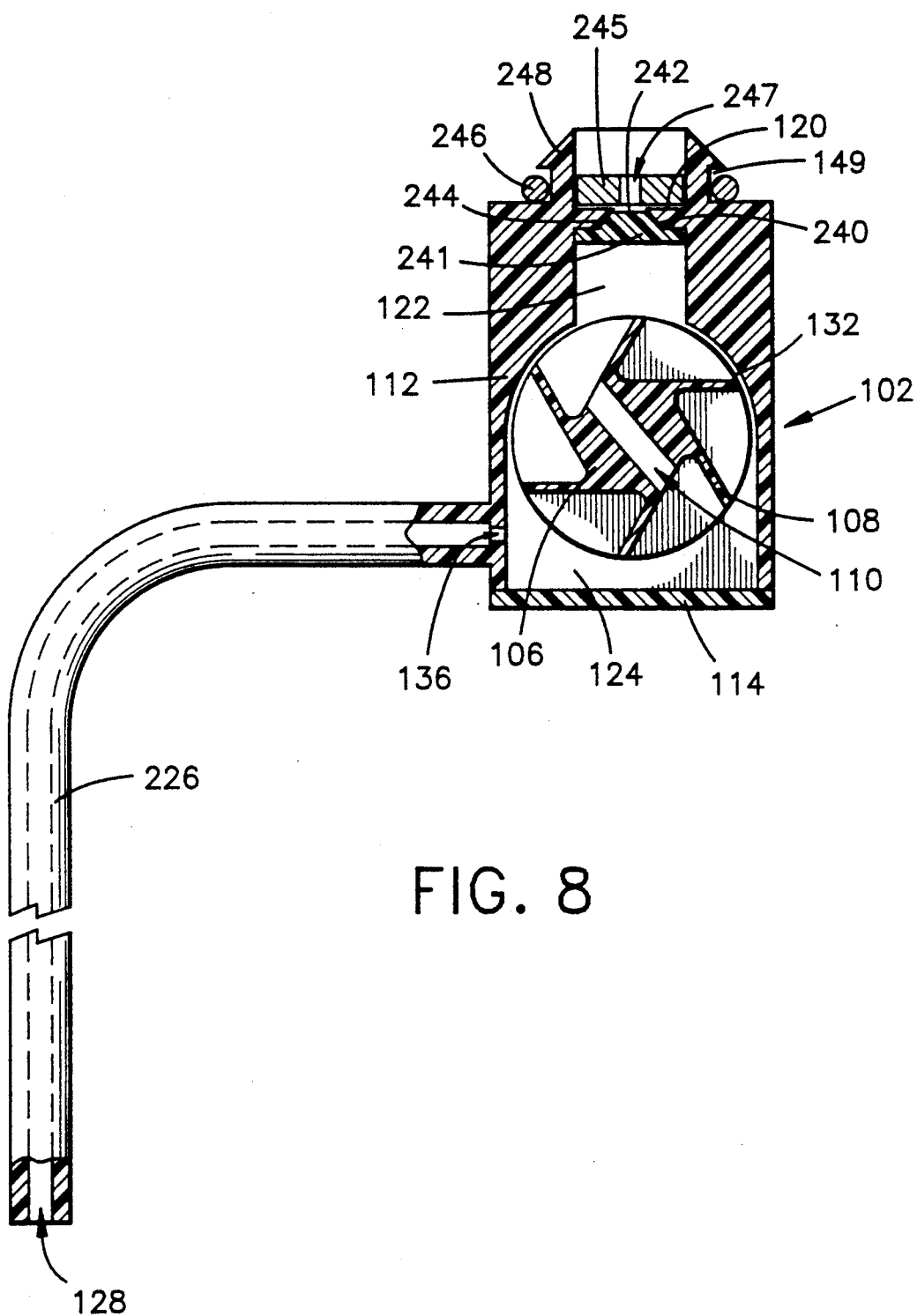
FIG. 8: is a cross section of the internal valve body and parts.

FIG. 8 is a modification of the valve of FIG. 7 to act as an internal pulsating valve in a pressurized container. Like parts numbers start at 100, unlike parts start at 200, and the valve is intended to be mounted on the top horizontal surface of a pressurized container. If it is mounted on the vertical surface, then the fluid pickup tube 226 would be straight. The parts that cause the valve in FIG. 8 to produce a pulsed stream and the mode of operation are identical to FIG. 7.

The internal valve body 112 is connected to the pressurized container by securing hooks 248 which pass through an opening in the wall of the pressurized container and are held in place by the hooks. An "O" ring 246 securely seals the contents of the container from leaking past the hooks 248.

The sealing plug 241 is held in place by the retaining flange 120 on the wall of the internal valve body 112. The plug sealing surface 244 rests securely against the flange sealing surface 240. The positive pressure inside the pressurized container causes the sealing plug 241 to jam itself against the plug sealing surface 244 without using a spring.

A non-pulsating external tip having all the parts described in FIG. 7, except the pulsating valve 2, is inserted into the can. In operation the tube 26 (not shown) of external pulsating valve body 12 (not shown) passes through the orifice 247 of the sealing washer 245. Pressing against the top of the sealing plug 242 causing the plug sealing surface 244 to move away from the flange sealing surface 240 allowing the pressurized fluid to travel around the sealing plug 241, through the notch 29 (not shown), up the channel 28 (not shown), through the interior of the external pulsating valve body 12 (not shown) to exit through the rotatable thin tube 16 (not shown).

Figure 9:
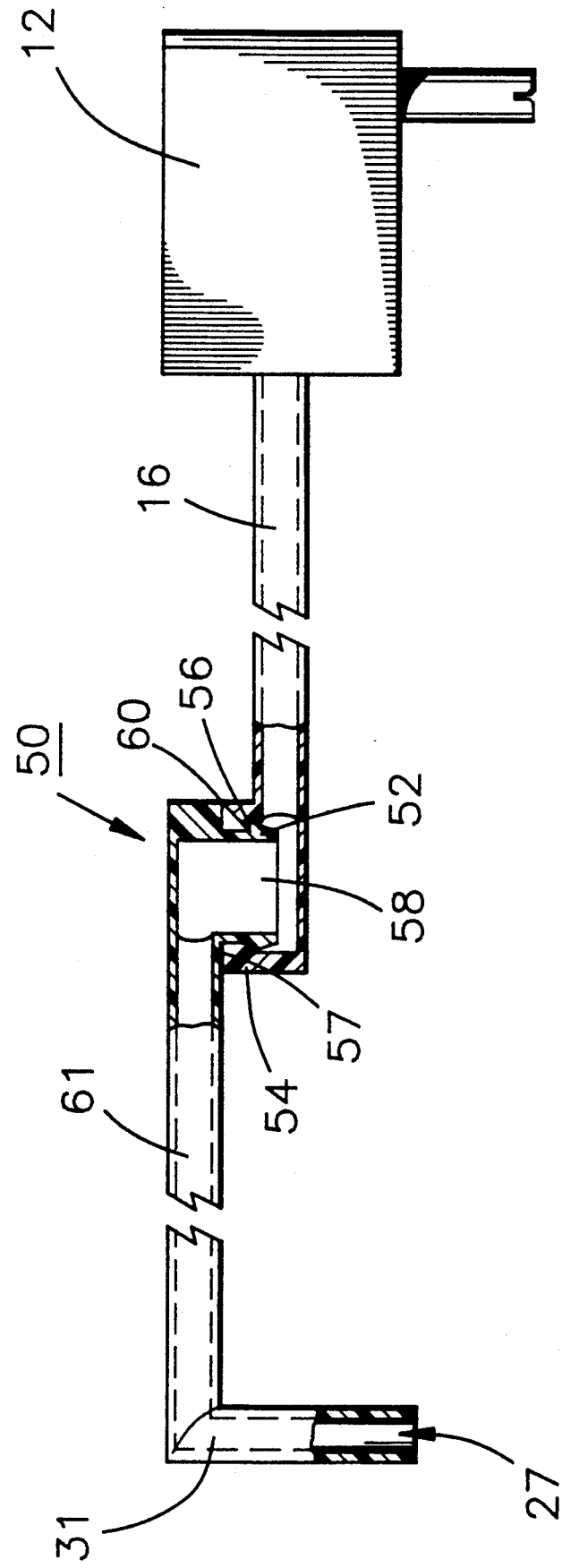
FIG. 9: is a cross section of the rotatable coupling for the rotatable thin tube.

FIG. 9 shows a construction of the rotatable thin tube 16 which allows it to be bent to any angle and to continue to pass fluid in an unobstructed manner. The thin rotatable tube 16 connects to the external pulsating valve body 12 as shown in FIG. 7. At a distance where the rotatable thin tube 16 clears the radius of the can a leak resistant rotatable joint 50 is provided so that the applicator tube 61 can lie flat against the pressurized container making it convenient to carry on one's person and to permit the tube to be covered by a protective device. The leak resistant rotatable joint 50 snaps together when the male securing hooks 52 on applicator tube 61 engage the female securing hooks 54 forming a common sealing surface 56. The female securing hooks 54, on the rotatable thin tube 16, have resilient points 60 which press against flat circular surface 57 located at the base of male securing hooks 52. This, in addition to the internal pressure in the common chamber 58, provides further pressure on the common sealing surface 56 to insure no leakage. It is also possible to place an "O" ring between the common sealing surface 56, if it were found necessary to prevent leakage.

In operation, the pressurized fluid from the can passes through the rotatable thin tube 16, through the leak resistant rotatable joint 50, directed by angle 31 to the discharge port 27 where the fluid exits.

In FIGS. 10, 11, and 12, a bottle (not shown) and the bottle's threads (not shown) engage the threads 84 of the bottle cap 82 and are screwed together. This causes the rim on the bottle to press the pulsating flexible valve 90 against the bottle cap 82 sealing the contents of the bottle. The fluid pickup tube 93 fits into the pulsating flexible valve 90 passing through the flexible valve port 94 whereby the pickup tube flange 95 is seated in a notch 91 in the pulsating flexible valve 90. It is to be understood that the bottle cap 82 could be secured to the bottle by any of a number of different methods. The method employed is not important to this invention. When the cleaning device is to be used the bottle is shaken, releasing the carbon dioxide gas, increasing the internal pressure of the bottle. When the external pulsating valve body 12 (not shown) is positioned at the top of the bottle cap 82 is depressed the tube 26 (not shown) presses against the top 98 of the tapered plug 92 located on the upper side of the pulsating flexible valve 90. The tapered plug 92 moves away from the valve seat 88 forming a depression in the area where the depression forms 96. This depression causes the fluid bypass holes 94 to move away from top inside surface of the bottle cap 99. Fluid flows through the fluid pickup tube 93 through the fluid bypass holes 94, following the depression in the area where the depression forms 96 to the exit port 86 and into the tube 26 (not shown). The flow of fluid between the pulsating flexible valve 90 and the top inside surface of the bottle cap 99 creates a low pressure area in the area where the depression forms 96 which will cause the pulsating flexible valve 90 to move closer to the top inside surface of the bottle cap 99 and the flow of fluid will be momentarily diminished. The pulsating flexible valve 90 will again move away from the top inside surface of the bottle cap 99 and the cycle will be repeated causing the flow of fluid to pulsate. The external pulsating valve body 12 may be used with or without the pulsating valve 2 in this configuration and still produce a pulsed stream. It will be understood that the bottle cap 82 could be combined with the internal valve body 112.

The various elements aof the present invention may be constructed of any suitable materials and by processes well known in the art.

It will thus been seen that the objects set forth above, among those made apparent from the preceding descriptions, are efficiently attained and, since certain changes may be made in the above constructions without departing from the scope of the invention, it is intended that all matter contained in the above descriptions or shown in the accompanying Drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

We claim:

1. A hand held, portable, oral cavity cleaning appliance that produces a pulsed stream of fluid, comprising:
    (a) input means, including an inlet channel, to receive said fluid under pressure;
    (b) output means to deliver said fluid to said oral cavity; and
    (c) pulsating means connected between said input means and said output means to provide said stream of fluid in a series of pulses, said pulsating means comprising:
        (i) a body;
        (ii) an at least partially cylindrical channel defined within said body transverse to the flow of said stream of fluid through said body;
        (iii) a close-fitting rotary valve disposed within said channel, said rotary valve comprising:
            (1) a cylindrical rotor coaxially aligned with the cylindrical portion of said channel;
            (2) a plurality of canted fins extending radially from the surface of said cylindrical rotor and axially between end pieces; and
            (3) a transverse channel defined through said cylindrical rotor generally orthogonal to the longitudinal axis thereof; and
    (d) an inlet opening defined in said body on one side of said rotary valve for the entry of said fluid into said body and an outlet opening defined in said body on the opposite side of said rotary valve for the exit of said fluid from said body;

whereby, said cylindrical rotor is caused to rotate when said fluid impinges on said fins after passing through said inlet opening and said pulses are produced by the intermittent passage of some of said fluid through said transverse channel as said cylindrical rotor rotates.

2. A cleaning appliance, as defined in claim 1, wherein said input means is adapted to be attached to a container containing said fluid and containing a gas under pressure greater than atmospheric pressure, thereby to receive said fluid from said container.

3. A cleaning appliance, as defined in, claim 1 wherein said output means includes means to direct said pulsed stream of fluid to the gums and teeth of the user.

4. A cleaning appliance, as defined in claim 3, wherein said means to direct said pulsed stream includes a rotatable joint for rotation thereof to a desired angle.

5. A cleaning appliance, as defined in claim 4, wherein the elements of said rotatable joint are snapped together.

6. A cleaning appliance, as defined in claim 3, wherein said means to direct said pulsed stream includes a discharge tube with an angled portion near the distal end of said tube.

7. A cleaning appliance, as defined in claim 6, wherein said discharge tube includes means to allow said discharge tube to rotate.

8. A cleaning appliance, as defined in claim 6, further comprising protection means to protect said appliance from contact with foreign matter, comprising:
   (a) shield means having top and bottom portions and a semi-flexible body portion extending therebetween;
   (b) said body portion having a cutout of sufficient size so that, when the edges of said cutout are spread apart, a pressurized can with said cleaning appliance mounted thereon can be inserted into said shield means and removed from said shield means;
   (c) said top portion having a cutout for access to operate said pulsating means; and
   (d) said shield means being rotatable to a first position to permit said discharge tube to be used and being rotatable to a second position to permit said discharge tube to be covered by said shield.

9. A cleaning appliance, as defined in claim 1, further comprising control means for controlling the flow of said fluid through said pulsating means.

10. A cleaning appliance, as defined in claim 9, wherein said control means comprises a resilient plug disposed in said input means, said plug being moveable between a closed position and an open position and, in said closed position, said plug is held against a sealing surface by the pressure of said fluid and, in said open position, said plug is biased away from said sealing surface, thereby to allow said fluid to flow into said body.

11. A cleaning appliance, as defined in claim 1, further comprising said body having a removable end plate to facilitate construction of said cleaning appliance.

12. A cleaning appliance, as defined in claim 1, wherein said appliance is temporarily attachable to a pressurized container of said fluid.

13. A cleaning appliance, as defined in claim 1, wherein said appliance is permanently attached to a pressurized container of said fluid.

14. A cleaning appliance, as defined in claim 1, wherein said pressurized container is a container of carbonated liquid.

15. A cleaning appliance, as defined in claim 1, further comprising a pickup tube extending downward from said fluid inlet channel.

16. A cleaning appliance, as defined in claim 11, further comprising protection means to protect said appliance from contact with foreign matter.

17. A cleaning appliance, as defined in claim 1, wherein said rotary valve further comprises end pieces sealing said rotary valve against the ends of said channel and bearing against said cylindrical portion of said channel.

18. A cleaning appliance, as defined in claim 1, wherein said input means comprises:
   (a) a bottle cap;
   (b) an orifice defined in the top of said bottle cap;
   (c) attachment means for attachment of said pulsating means to said bottle cap such that said liquid may be suppled to said pulsating means through said orifice; and
   (d) control means to control the flow of said liquid through said orifice.

* * * * *